United States Patent
Walls

(10) Patent No.: US 9,375,289 B1
(45) Date of Patent: Jun. 28, 2016

(54) INTRA-ORAL DEVICE

(71) Applicant: Laura Driessen Walls, Carlsbad, CA (US)

(72) Inventor: Laura Driessen Walls, Carlsbad, CA (US)

(\*) Notice: Subject to any disclaimer, the term of this patent is extended or adjusted under 35 U.S.C. 154(b) by 0 days.

(21) Appl. No.: 14/968,163

(22) Filed: Dec. 14, 2015

Related U.S. Application Data

(60) Provisional application No. 62/098,040, filed on Dec. 30, 2014.

(51) Int. Cl.
*A61C 5/00* (2006.01)
*A61C 7/08* (2006.01)
*A61F 5/56* (2006.01)

(52) U.S. Cl.
CPC . *A61C 5/007* (2013.01); *A61C 7/08* (2013.01); *A61F 2005/563* (2013.01)

(58) Field of Classification Search
CPC ....................................................... A61F 5/566
See application file for complete search history.

(56) References Cited

U.S. PATENT DOCUMENTS

| | | | | |
|---|---|---|---|---|
| 2005/0166929 A1* | 8/2005 | Jiang | ....................... | A61F 5/566 128/861 |
| 2005/0236003 A1* | 10/2005 | Meader | ................... | A61F 5/566 128/848 |
| 2008/0138766 A1* | 6/2008 | Jansheski | ................. | A61C 7/08 433/140 |
| 2014/0261465 A1* | 9/2014 | Turkbas | ............... | A63B 71/085 128/862 |

\* cited by examiner

*Primary Examiner* — Nicholas Woodall
*Assistant Examiner* — Tarla Patel
(74) *Attorney, Agent, or Firm* — Eric Hanscom; Todd J. Langford

(57) ABSTRACT

A mouthpiece of medical grade silicone that has two connecting portions, one a molded shallow trough that wraps around and contours the teeth, and another a flap or wing portion that attaches to the front of the shallow trough and that acts to sit between and keep separate the teeth and lips.

11 Claims, 4 Drawing Sheets

INTRA-ORAL DEVICE

CROSS REFERENCE TO RELATED APPLICATIONS

This application claims priority back to U.S. Provisional Application No. 62/098,040, filed Dec. 30, 2014, the contents of which are incorporated by reference.

STATEMENT REGARDING FEDERALLY SPONSORED RESEARCH OR DEVELOPMENT

This invention was not federally sponsored.

BACKGROUND OF THE INVENTION

Field of the Invention

This invention relates to the general field of intra-oral devices, and more specifically toward a mouthpiece that has two connecting portions, one a molded shallow trough that wraps around and contours the teeth, and another a flap or wing portion that attaches to the front of the shallow trough and that acts to sit between and keep separate the teeth from the cheeks and lips.

Oral appliances are typically shaped in various ways, which include, but are not limited to, a holder in the shape of a curved tray that is made of moldable, semi-rigid polymeric material and a holder in the shape of a curved palate that is made of rigid polymeric material, thermal urethane and metal bonds. Such appliances are used in a variety of applications such as bite guards to treat Bruxism or clenching, snore prevention devices, and mouth guards to correct dental alignment and temporomandibular joint dysfunction (TMJD) and improve and retain correct swallowing patterns. The structure of the present disclosure is described in particular relationship to a mouth guard designed to 1) improve and retain dental alignment and occlusion, 2) reduce jaw tension, 3) encourage the tongue to stay on the anterior alveolar ridge/incisive papilla, 4) promote a proper breathing and mouth placement and to 5) correct swallowing patterns.

Several mouth guard devices are available commercially for use by dentists, orthodontists and direct consumers. With existing mouth guard appliances, typically the appliance is constructed from one base material—the semi-rigid polymeric material. The consumers place a semi-rigid mouth guard appliance in boiling water and, once the semi-rigid material has softened, insert the appliance in their mouths over their upper and/or lower jaw, allowing the softened material to set and shape the mouth guard around their teeth. Any excess material that does not fit within the consumers' mouths is trimmed away to provide the wearer with a comfortable appliance. However, this structure is limiting. Consumers are required to fit the appliance to their mouth on their own. Any small error when forming the mouth guard around the teeth will lead to discomfort, an improper (and therefore ineffective) fit, and/or additional expense, as the consumer will be required to either purchase a replacement appliance or consult with a professional for an adjustment. Also, since the appliance is made from one base material, it can either be overly hard or overly soft. Overly hard materials provide the consumer a rigid appliance with limited comfort while being worn. A softer material is comfortable yet has insufficient force needed to correct the wearer's swallowing pattern. Other mouth guard appliances that are not made of moldable material typically require a fitting from a professional dentist or orthodontist. The rigid material is painful in the consumer's mouth and also the initial cost to fit the mouth guards is expensive. Additionally, mouth guards that are permanent in a consumer's mouth, such as a lower fixed retainer, often result in improper tongue placement, creating poor swallow patterns, increased mouth breathing, and chance for malalignment.

Thus, mouth guard appliances that require molding by individuals, particularly general consumers, often result in an uncomfortable fit and additional costs for dental care professionals is required to fit the device properly or treat compounding issues. Mouth guard appliances that require molding and fittings for the consumer by professionals are expensive and can also result in additional jaw issues and do not address the root cause of the problem. These additional issues occur if the appliance is fit incorrectly, the position leads to improper jaw and tongue placement (such as the fixed retainer) or the tightness of the appliance causes strain and tension on the mouth and surrounding muscles. Therefore, there exists a need for an improved oral appliance that is multi-functional, effectively eliminating tongue thrust, malocclusions, Bruxism, and TMJD, while correcting the wearer's swallowing pattern. As well, the improved oral appliance will fit the consumer's mouth properly, yet be relatively inexpensive and comfortable.

SUMMARY OF THE INVENTION

The current disclosure provides an intra-oral device made of medical grade silicone that is in the shape of a mouth piece and is flexible and comfortable when placed in the user's mouth. The oral appliance has two connected portions, one that lays flat against the outside of the user's teeth, and one shallow trough that rests between the consumer's teeth. The flat portion has holes that allow for the user to breathe while wearing the oral appliance. The oral appliance is designed with the trough already molded to match a correct teeth alignment, with the purpose that the user's teeth will rest on that trough and conform to the correct position over time. Also, with the trough already molded, the user does not need to go through the process of molding the appliance herself. The trough also is fitted with indicator marks for the professional or user to trim off any section that does not fit within their mouth. Since the material has indication marks, the cutting is simple. The flat portion of the oral appliance also has indication marks for cutting off any excess portions that do not fit within the user's mouth.

The intra-oral device of the current disclosure is superior to other intra-oral devices due at least in part to its composition, design and use. The device is made of medical grade silicone plastic. The design of the device helps support body/sleep posture, jaw, cheek, lip, and tongue position and placement with a sleek, removable mouth piece.

The intra-oral device has no outer plastics to support outside facial structures. It is unobtrusive and not visible to others. In a particular embodiment, it is used to train intranasal breathing in an effort to promote relaxation and lessen contact with airborne infections/viruses. Air holes are incorporated to provide access when changing to intranasal or during times of congestion, thereby enabling use with rhinovirus/allergy symptoms. A particular design of the current intra-oral device enables it to be coupled with retainers, braces, and rubber bands, including clear braces, Invisalign brand retainers, and braces. Furthermore, it can lessen jaw tension and effects of TMJD while retaining teeth posture. The device adjusts anterior tongue placement to promote a good oral swallowing pattern.

Use of the intra-oral device disclosed herein can help prevent Bruxism. The device has wings that extend to the back molars of an individual to prevent or reduce the effects of linea alba (which is caused by ill fitting dentures, orthodontic appliances, or crooked or broken teeth). External buccal wings and bite surface extend to the second molar, preventing linea alba. The device can be used to prevent suckling and has air holes to allow natural oral breath. The device has winged cheek separators to pull the cheek away from the teeth. Internal wings promote lip closure and relaxed facial muscles. No head strap is required for proper use of the device. The intra-oral device can even be used for sleep apnea and snoring.

By elevating the tongue, the jaw will naturally come forward, allowing the muscles to relax, and enable an appropriate swallow function all while encouraging lateral tongue muscle engagement and providing dental stability and placement maintenance. Suckling of the cheeks, causing dental inversion, will be eliminated by the intra-oral device disclosed herein. Furthermore, grinding is eliminated by the proper use of the intra-oral device, while also allowing for the lips to remain closed while using the intra-oral device. The intra-oral device postures the jaw, lips, cheek and tongue into proper position and it allows dentition to remain straight. The velum is allowed to relax, while increasing intranasal breath and decreasing pharyngeal tension related to snoring and mild sleep apnea thereby addressing oral dissociation, breathing, and snoring.

Embodiments of the intra-oral device disclosed herein allow neutral jaw position and appropriate space between upper and lower teeth, which addresses freeway space. It protects the teeth from clenching and grinding (Bruxism) of the upper and lower dentition, and facilitates relaxed jaw muscles to reduce symptoms of TMJD and lock jaw. It provides stability of the upper and lower dentition to prevent/reduce gum recession before and after surgery (gingival recession). Furthermore, it separates the cheeks from the upper/lower molars, thereby preventing linea alba, molar inversion related to suckling, and cheek abrasion from sucking. The intra-oral device prevents incisal movements, suckling and swallowing difficulties and promotes correct tongue placement at the anterior incisive papilla. Additionally, it stabilizes and balances the temporal mandibular joints, bilaterally promoting adequate intra-oral posture for proper swallowing and can be used to lessen pterygoid and masseter tension or spasms. Furthermore, it promotes muscle relaxation.

It is an object of the current disclosure to provide an intra-oral device to improve and retain dental alignment, correct swallowing patterns, and improve proper breathing and mouth placement.

It is another object of the current disclosure to provide an intra-oral device that eliminates tongue thrust and reduces mild sleep apnea and snoring.

It is a further object of the current disclosure to provide an intra-oral device that lessens the effects of Bruxism, clenching, and TMJD, and improves dental retention.

It is an additional object of the current disclosure to provide an intra-oral device that promotes long-term use while remediating TMJD and tongue thrust.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration. As used herein, an intra-oral device includes an oral appliance and oral orthotic.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE FIGURES

The accompanying drawings, which are incorporated in and form a part of this specification, illustrate embodiments of the invention and together with the description, serve to explain the principles of this invention.

DETAILED DESCRIPTION OF THE INVENTION

Figure 1:
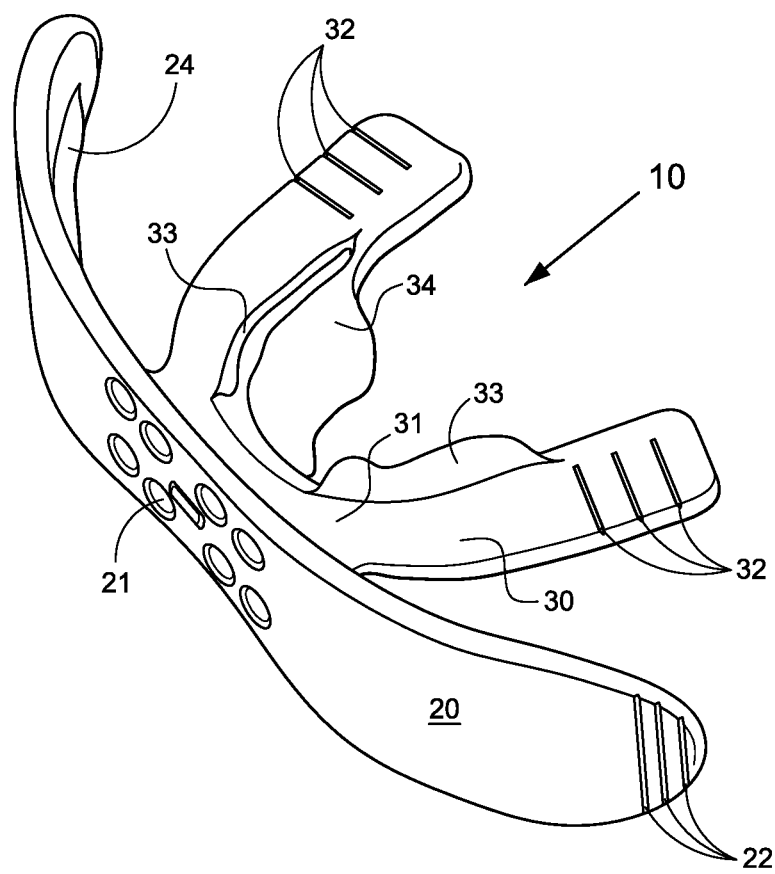
FIG. 1 is a perspective view of an intra-oral device according to selected embodiments of the current disclosure.

Many aspects of the invention can be better understood with the references made to the drawings below. The components in the drawings are not necessarily drawn to scale. Instead, emphasis is placed upon clearly illustrating the components of the present invention. Moreover, like reference numerals designate corresponding parts through the several views in the drawings.

FIG. 1 is a perspective view of an intra-oral device according to selected embodiments of the current disclosure. The intra-oral device 10 has two main portions, a front portion 20 and a flat, back portion 30. The front portion 20 lays flat against the outside of the user's teeth. The front portion also has holes 21 that allow for a user to breathe while wearing the oral appliance. The holes 21 provide openings through which air may pass such that a user can inhale and exhale when the intra-oral device is properly in place between the teeth of the user. The edges of the front portion include indicator marks 22. The indicator marks are used for customizing the intra-oral device 10 for a particular user's mouth. A user cuts off sections of the front portion along the indicator marks 22, thereby customizing the size of the intra-oral device to fit properly and comfortably within the user's mouth. A bulge 24 runs along the back side of the front portion 20 to provide additional support to the front portion 20.

The back portion 30 fits between the teeth of the user. The back portion 30 of the intra-oral device 10 is designed with a trough 31 already molded to match a user's correct teeth alignment, with the purpose that the user's teeth will rest within that trough 31 and conform to the correct position over time. The back portion 30 includes an upper wall 33 and lower wall 34 that help form the trough 31. To assist in customizing the intra-oral device for a particular user's mouth, indicator marks 32 are also included in the back portion 30. As with the indicator marks of the front portion, users can cut off sections of the back portion along the indicator marks, thereby customizing the size of the intra-oral device to fit properly and comfortably within the user's mouth.

Figure 2:
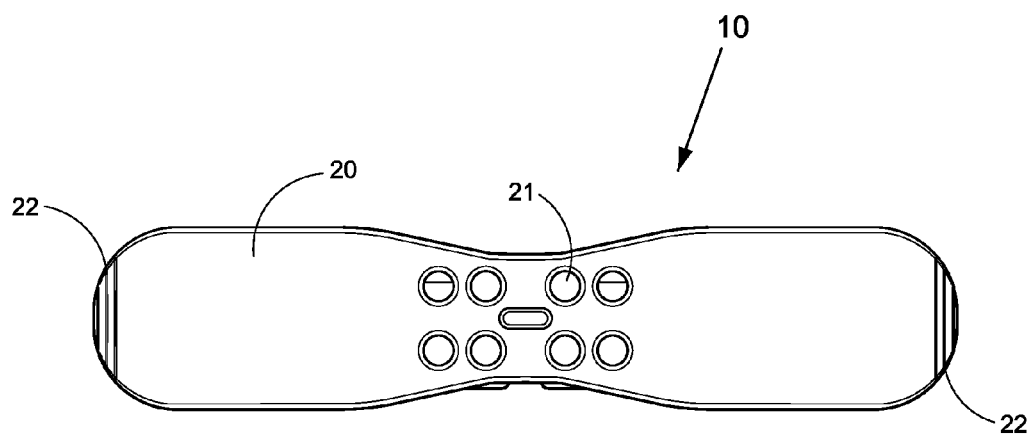
FIG. 2 is a front view of an intra-oral device according to selected embodiments of the current disclosure.

FIG. 2 is a front view of an intra-oral device according to selected embodiments of the current disclosure. The intra-oral device 10 has holes 21 in the front portion 20. As shown in this figure, particular embodiments of the current disclosure provide for eight holes 21, with four holes each on the top and the bottom, and four holes each on the left and the right. The holes 21 are circular in shape. While eight holes in the configuration above may be preferable, other configurations with greater or fewer holes are possible without departing from the scope of the current disclosure. The front portion 20 has rounded outer edges with indicator marks 22. The middle of the front portion 20, is tapered such that the height of the front portion is smaller.

Figure 3:
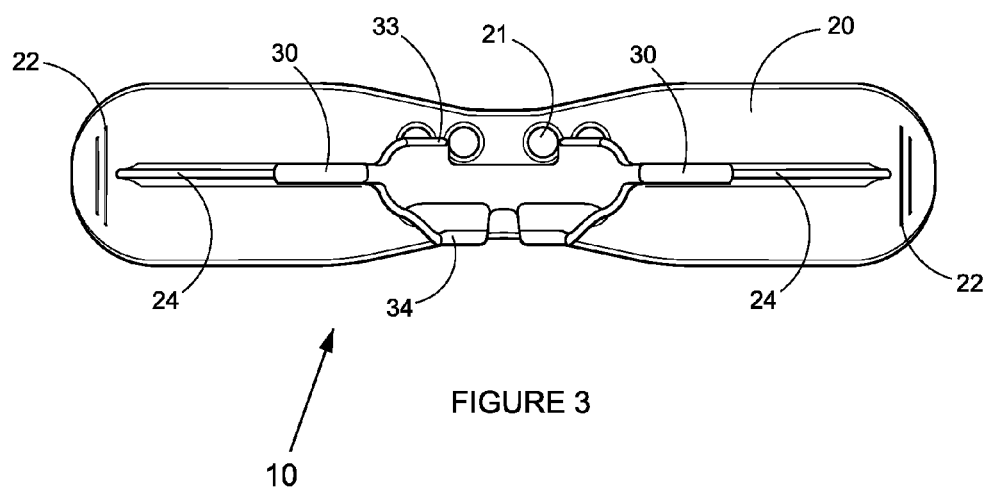
FIG. 3 is a back view of an intra-oral device according to selected embodiments of the current disclosure.

FIG. 3 is a back view of an intra-oral device according to selected embodiments of the current disclosure. Indicator marks 22 are shown on the back side of the front portion along the intra-oral device's 10 outer areas. There is a gap in the upper wall 33 towards the front of the back portion 30. The lower wall 34 also has a gap therein, but smaller than the gap in the upper wall 33. The intra-oral device 10 has holes 21 in the front portion 20. A bulge 24 runs along the back side of the front portion 20 to provide additional support to the front portion 20.

Figure 4:
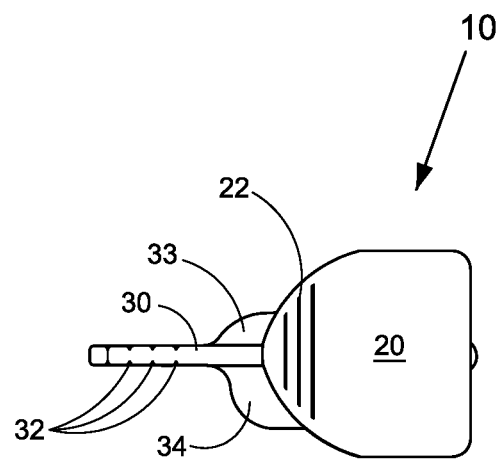
FIG. 4 is a left side view of an intra-oral device according to selected embodiments of the current disclosure.
Figure 5:
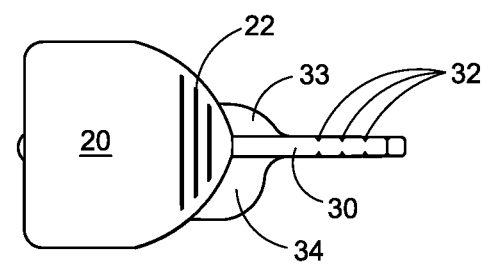
FIG. 5 is a right side view of an intra-oral device according to selected embodiments of the current disclosure.

FIG. 4 is a left side view of an intra-oral device according to selected embodiments of the current disclosure. FIG. 5 is a right side view of an intra-oral device according to selected embodiments of the current disclosure. The back portion extends away from the front portion, and is substantially perpendicular to the front portion. There are three indicator marks 22 shown on either side of the front portion 20 of the intra-oral device 10, however one skilled in the art should appreciate that more or less than three indicator marks 22 can be placed on the front portion. The back portion 30 includes an upper wall 33 and lower wall 34 that help form the trough. Each side of the back portion 30 of the intra-oral device 10 includes three indicator marks 32 that are present on both the top and the bottom of the back portion. However, one skilled in the art should appreciate that more or less than three indicator marks 32 can be placed on the back portion 30.

Figure 6:
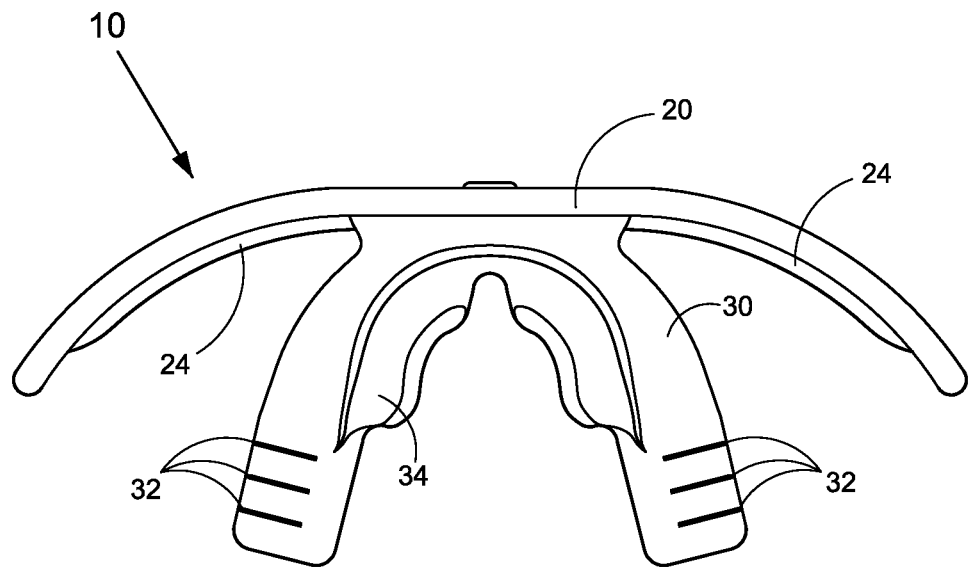
FIG. 6 is a bottom view of an intra-oral device according to selected embodiments of the current disclosure.
Figure 7:
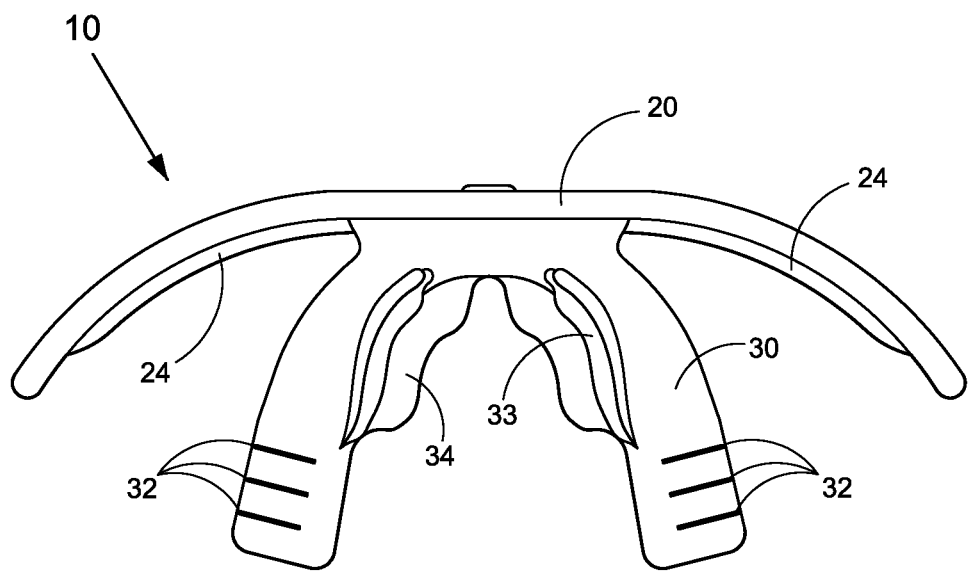
FIG. 7 is a top view of an intra-oral device according to selected embodiments of the current disclosure.

FIG. 6 is a bottom view of an intra-oral device according to selected embodiments of the current disclosure. FIG. 7 is a top view of an intra-oral device according to selected embodiments of the current disclosure. Each side of the back portion 30 of the intra-oral device 10 includes three indicator marks 32 that are present on both the top and the bottom of the back portion. However, one skilled in the art should appreciate that more or less than three indicator marks 32 can be placed on the back portion 30. The front portion 20 has ends that curve towards the back portion. The back portion 30 includes an upper wall 33 and lower wall 34 that help form the trough. A bulge 24 runs along the back side of the front portion 20 to provide additional support to the front portion 20.

In a particular embodiment of the intra-oral device, the trough is shaped in the position of a correct teeth alignment, with the purpose that the user's teeth will rest within that trough and conform to the correct position over time.

The intra-oral device disclosed herein improves and retains dental alignment, corrects swallowing patterns, and improves proper breathing and mouth placement. As it is a multi-functional oral appliance, it also effectively eliminates tongue thrust, malocclusions, Bruxism, and TMJD, while providing the user with a proper and comfortable fit at a relatively inexpensive cost.

A particular embodiment of the current disclosure provides for an intra-oral device that is made at least partially from medical grade silicone. In another embodiment, the intra-oral device is made entirely from medical grade silicone.

The intra-oral device as disclosed herein can be customized for an individual user by removing parts of the front portion and/or back portion. A user may cut one or both sides of the front portion or back portion along the indicator marks. Scissors, a knife, or other cutting instrument can be used to aid the user in cleanly cutting portions of the front portion and/or back portion.

In a particular embodiment, a user will place the unaltered intra-oral device within her mouth. If the intra-oral device is determined to be too big, such as in the front portion, the back portion, or both, the user removes the intra-oral device and removes a portion of the intra-oral device along one or more of the indicator marks. The user then places the altered intra-oral device within her mouth. If the intra-oral device is still determined to be too big or of improper shape, the user once again removes the intra-oral device and removes another portion of the intra-oral device along one or more of the remaining indicator marks. The user then places the altered intra-oral device within her mouth. The process is repeated until an appropriately sized and shaped intra-oral device is made for the user, removing small portions of the intra-oral device along the indicator marks during each iteration.

To use the intra-oral device, a user places the intra-oral device in her mouth such that the teeth are aligned with and rest on the trough. Over time, the teeth of the user conform to the correct position. In a particular embodiment, the user places the intra-oral device in her mouth for a set period of time on a regular schedule, such as during the night while she sleeps. Through such use, the intra-oral device improves and retains dental alignment, corrects swallowing patterns, and improves proper breathing and mouth placement. As it is a multi-functional oral appliance, it also effectively eliminates tongue thrust, malocclusions, Bruxism, TMJD, and snoring/sleep apnea, while providing the user with a proper and comfortable fit at a relatively inexpensive cost.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims are regarded as the invention.

That which is claimed:

1. An intra-oral device consisting of:
a front portion and a back portion;
wherein the front portion comprises a middle section and two end sections, wherein the middle section comprises a number of holes, wherein the number of holes comprises eight holes, and wherein each of the two end sections comprises a number of indicator marks, wherein the number of indicator marks comprises at least one indicator mark, wherein each of the number of indicator marks comprises a slot in its respective end section, wherein a user of the intra-oral device can cut the device at one or more of the indicator marks to fit the device for a mouth of a particular user,
wherein the front portion is connected to the back portion;
wherein the back portion comprises an upper wall, and a lower wall, and a plurality of indicator marks, wherein the upper wall comprises a gap, and wherein the lower wall comprises a gap, wherein the back portion has two projections that have a shape and separation of roughly an average bite of a human, and wherein each of the two projections has a terminal end section, and wherein each terminal end section additionally comprises a number of indicator marks, wherein the number of indicator marks comprises at least one indicator mark, wherein each of the number of indicator marks comprises a slot in its respective terminal end section, wherein a user of the intra-oral device can cut the device at one or more of the indicator marks of the terminal end sections of the back portion to fit the device for a mouth of a particular user, and, wherein the intra-oral device is made entirely from medical grade silicone.

2. An intra-oral device comprising
a front portion and a back portion;
wherein the front portion comprises a middle section and two end sections, wherein the middle section comprises a number of holes, wherein the number of holes comprises eight holes, and wherein each of the two end sections comprise a number of indicator marks, wherein the number of indicator marks comprises at least one indicator mark, wherein each of the number of indicator marks comprises a slot in its respective end section, wherein a user of the intra-oral device can cut the device at one of the indicator marks to fit the device for a mouth of a particular user,
wherein the front portion is connected to the back portion;
wherein the back portion comprises an upper wall, and a lower wall, and a plurality of indicator marks, wherein the upper wall comprises a gap, and wherein the lower wall comprises a gap, wherein the back portion has two projections that have a shape and separation of roughly an average bite of a human, and wherein each of the two projections has a terminal end section, and wherein each terminal end section additionally comprises a number of indicator marks, wherein the number of indicator marks comprises at least one indicator mark, wherein each of the number of indicator marks comprises a slot in its respective terminal end section, wherein a user of the intra-oral device can cut the device at one or more of the indicator marks of the terminal end sections of the back portion to fit the device for a mouth of a particular user, and, wherein the intra-oral device is made entirely from medical grade silicone.

3. An intra-oral device comprising
a front portion and a back portion;
wherein the front portion comprises a middle section and two end sections, wherein the middle section comprises one or more holes, and wherein each of the two end sections comprise at least one indicator mark, wherein each of the indicator marks comprises a slot in its respective end section, wherein a user of the intra-oral device can cut the device at one or more of the indicator marks to fit the device for a mouth of a particular user,
wherein the front portion is connected to the back portion;
wherein the back portion comprises an upper wall, and a lower wall, and a plurality of indicator marks, wherein the upper wall comprises a gap, and wherein the lower wall comprises a gap, wherein the back portion has two projections that have a shape and separation of roughly an average bite of a human, and wherein each of the two projections has a terminal end section, and wherein each terminal end section additionally comprises at least one indicator mark, wherein each indicator mark comprises a slot in its respective terminal end section, wherein a user of the intra-oral device can cut the device at one or more of the indicator marks of the terminal end sections of the back portion to fit the device for a mouth of a particular user.

4. The device of claim 3, wherein the middle section of the front portion comprises eight holes.

5. The device of claim 3, wherein the middle section of the front portion comprises fewer than eight holes.

6. The device of claim 3, wherein the intra-oral device is made at least partially from medical grade silicone.

7. The device of claim 3, wherein the intra-oral device is made entirely from medical grade silicone.

8. The device of claim 3, wherein the device is made at least partially from thermoplastic material.

9. The device of claim 3, wherein the device is made entirely from thermoplastic material.

10. The device of claim 3, wherein the number of indicator lines in each of the two end sections of the front portion is three.

11. The device of claim 3, wherein the number of indicator lines in each of the terminal end sections of the back portion is three.

* * * * *